United States Patent [19]

Ho et al.

[11] Patent Number: 4,923,895

[45] Date of Patent: May 8, 1990

[54] METHOD OF TREATMENT OF HUMAN IMMUNODEFICIENCY VIRUS

[75] Inventors: Monto Ho; Phalguni Gupta, both of Pittsburgh, Pa.

[73] Assignee: University of Pittsburgh of the Commonwealth System of Higher Education, Pittsburgh, Pa.

[21] Appl. No.: 261,680

[22] Filed: Oct. 24, 1988

[51] Int. Cl.$^5$ ............................................ A61K 31/285
[52] U.S. Cl. ................................................... 514/504
[58] Field of Search ......................................... 514/504

[56] References Cited

U.S. PATENT DOCUMENTS 986,148  3/1911  Ehrlich et al. ...................... 514/504

OTHER PUBLICATIONS

Chemical Abstracts 77: 1122982, (1972).

Primary Examiner—Jerome D. Goldberg
Attorney, Agent, or Firm—Arnold B. Silverman; Rita M. Rooney

[57] ABSTRACT

A method of treating a patient for human immunodeficiency virus (HIV) includes administering to the individual patient intravenously a therapeutically effective dosage of oxyphenarshine (3 amino-4 hydroxyphenylarsineoxide hydrochloride). The dose emplyed may be up to about 1 milligram per kilogram of body weight administered 1 to 2 times weekly. The oxyphenarsine is preferably administered in such an amount as to achieve in said patient a blood serum concentration of about 0.12 to 6.0 micrograms per milliliter.

8 Claims, No Drawings

METHOD OF TREATMENT OF HUMAN IMMUNODEFICIENCY VIRUS

BACKGROUND OF THE INVENTION

1. Field of the Invention

The present invention relates to a method of treating a patient for human immunodeficiency virus and, more specifically, a method of intravenously administering an organic arsenical for treatment of human immunodeficiency virus type 1. 2. Description of the Prior Art It has been known to employ organic arsenicals for therapeutic purposes. See, for example, U.S. Pat. No. 986,148.

It has also been known to employ oxyphenarsine (3 amino-4 hydroxyphenyl-arsineoxide hydrochloride) in the treatment of syphilis.

Human immunodeficiency virus type 1 or HIV causes acquired immunodeficiency syndrome ("AIDS") and is a fatal disease which has approached epidemic proportions both within the U.S. and elsewhere. The problem has reached sufficiently serious proportions that by Executive order, the President of the U.S. established Presidential Commission on the Human Immunodeficiency Virus Epidemic.

HIV-infected individuals may remain asymptomatic for several years. By current estimates about 15-34% of infected individuals will probably develop AIDS within 3-5 years. During the asymptomatic stage, although most people have no symptoms, some patients a few weeks after exposure develop a disorder resembling mononucleosis. Later, its symptoms include fatigue, fever and swollen glands, diarrhea and minor infections. Most of these symptoms disappear initially but may recur. When AIDS develops, it is usually characterized by a major opportunistic infection, such as Pneumocystis pneumonia, or an opportunistic tumor, such as Kaposi's sarcoma or a lymphoma. At this stage, the disease is uniformly fatal.

While many drugs have been tried for the treatment of HIV and AIDS, no curative drug has been found.

One known drug, azidothymidine, was approved by the FDA in 1987. It relieves symptoms and prolongs life in the short run.

SUMMARY OF THE INVENTION

The present invention provides a method of treatment of human immunodeficiency virus (HIV).

In the practice of the present invention, a patient is treated for a human immunodeficiency virus by administering to the individual intravenously a therapeutically effective dosage of oxyphenarsine which is 3 amino-4 hydroxyphenyl-arsineoxide hydrochloride. The dosage is preferably administered in an amount of about up to 1 milligram per kilogram of body weight and more preferably about 0.5 to 1 milligram per kilogram of body weight. Smaller doses are given initially and gradually increased until the full dosages are attained. The drug preferably is given rapidly, intravenously at least 1 to 2 times per week depending on patient tolerance. The duration of treatment will generally be monitored by the anti-viral effect and tolerance. It is an object of the present invention to provide a method for treating human immunodeficiency virus which is efficient and employs a previously known compound. It is another object of the present invention to provide such a method of treatment which is safe and employs a compound which can be tolerated by the patient.

These and other objects of the invention will be fully understood from the following description of the invention.

DESCRIPTION OF THE PREFERRED EMBODIMENTS

The term "patient" as used herein shall mean a human being.

Oxyphenarsine which is 3 amino-4 hydroxyphenylarsineoxide hydrochloride is a trivalent organic aresenical drug which many years ago was successfully employed in the treatment of syphilis. The use of oxyphenarsine for this purpose was superseded by penicillin.

The AIDS virus is known to replicate in cultured lymphocytes of peripheral blood or in H9 cells which is a continuous line of human T lymphocytes. The standard laboratory assay of HIV in such HIV infected cultures is to monitor the production of p24, which is a major internal virion protein of HIV, in the culture fluid.

At concentrations of about 0.12 to 6.0 micrograms per ml, oxyphenarsine completely inhibits HIV infection of lymphocytes and H9 cells, and suppresses HIV production from cultured lymphocytes derived from HIV-infected individuals. Evidence of inhibition of replication was evident at concentrations as low as 0.035 to 0.7 micrograms per ml. At these concentrations, the kinetics of virus replication indicated by production of p24 is either undetected or reduced. At about 1.2 to 6.0 micrograms per ml the drug also inhibits the production of HIV in H9 cells persistently infected with HIV.

At concentrations of 0.6 microgram per ml or below, the drug has no toxicity, but at concentrations of about 1 to 6 micrograms per ml, there is evidence of mild inhibition of cell multiplication in both peripheral blood lymphocytes and H9 cells as monitored by uptake of titrated thymidine. In persistently infected H9 cells, the drug has no cytotoxic effect at 1.2 microgram per ml and has only mild inhibition of cell growth at 6 microgram per ml. At 60 milligrams per ml, the cells were destroyed.

At the range of concentrations at which HIV is inhibited, the drug is not toxic.

In its broader ranges the oxyphenarsine may be administered so that serum concentrations in a range of about 0.035 to 6.0 micrograms per ml in the blood stream may be desirable. Such concentrations are believed to be reached by the dosage set forth herein.

$5 \times 10^6$ phytohemagglutin (PHA)-stimulated normal peripheral blood lymphocytes or H9 cells were treated with DEAE-Dextran (25 microgram per ml) for 20 min at 37° C. Cells were then infected with 1 ml of cell free HIV ($2 \times 10^5$ reverse transcriptase unit) for 1 hr at 37° C. Cells were then washed and incubated for 12 days in the absence and presence of oxyphenarsine at concentrations ranging from 0.004 microgram per ml to 6 microgram per ml. Presence of HIV in the culture supernatant was monitored by measuring HIV p24 using the antigen capture test (Dupont, Wilmington, Del.). Results indicate that oxyphenarsine inhibited in vitro HIV infection in a dose dependent manner and that inhibition was detectable at concentration of 0.035-0.07 microgram per ml. Complete inhibition of HIV production was obtained at doses of 0.15 microgram per ml or higher.

The cytotoxic effect of the drug on PHA stimulated peripheral blood lymphocytes and on H9 cells was also examined. The drug at a concentration of 0.6 microgram per ml or lower had no cytopathic effect as judged by the measurement of the ($^3$H) thymidine uptake or of viable cell numbers. At concentrations of 1.2-6 microgram per ml, the drug had low levels of cytotoxic effect. At a concentration of 60 microgram per ml it was highly toxic for cells.

The drug did not have direct inhibitory effects on in vitro HIV reverse transcriptase activity at concentrations ranging from 0.006 to 60 microgram per ml. This is contrary to the behavior of azidothymidine which does serve as an inhibitor of HIV reverse transcriptase activity.

The effect of oxyphenarsine on the HIV production from lymphocytes of HIV seropositive patients was also examined. For this purpose, lymphocytes from an AIDS patient and a seropositive asymptomatic individual were cocultured with PHA stimulated PBL in the presence or absence of oxyphenarsine. Oxyphenarsine was found to inhibit HIV production from lymphocytes of both patients in a dose dependent manner. Virus production, as determined by the HIV p24 antigen capture assay, was completely blocked by oxyphenarsine at concentrations of 0.6 microgram per ml or higher. In contrast, HIV was detected in untreated cultures as early as 7 days following cocultivation. The inhibitory effect of the drug on HIV DNA synthesis was also examined in coculture experiment. The drug at concentrations 0.6 microgram per ml and 6.0 microgram per ml also had a significant inhibitory effect on the synthesis of HIV DNA in seropositive patient's lymphocytes cocultured with PHA-stimulated normal lymphocytes.

The effect of oxyphenarsine on the production of HIV was also examined in H9 cells persistently infected with HIV. $5 \times 10^6$ HIV-infected H9 cells were cultured in the absence and presence of 6.0 microgram per ml and 0.6 microgram per ml of oxyphenarsine. Every 4-5 days interval, two-thirds of the total cells were removed and the medium was changed. New medium with or without drug was added to bring up to the original volume. At regular intervals culture supernatant was withdrawn and tested for the production of HIV by the antigen capture test, by the reverse transcriptase activity and by the in vitro infectivity assay in PHA-stimulated PBL. We found that the amount of HIV present in the culture fluid, as determined by the presence of HIV p24, was greatly reduced in drug treated cultures as compared to the untreated control. Moreover, the culture fluids from oxyphenarsine-treated cells showed no significant levels of the reverse transcriptase activity nor infectious HIV within 4-7 days following the addition of the drug to the culture. In contrast, fluids from the untreated control cultures showed significant levels of reverse transcriptase activity and in vitro infectivity throughout the incubation period.

Oxyphenarsine is a drug which was used for many years against syphilis with well known but generally tolerable side effects. Locally it may produce phlebitis. Reactions most frequently observed are transitory nausea, vomiting, lacrimation, and pruritis. Mild dermatitis may occur. As with other arsenicals, the patient should be followed for hepatic and hemopoietic toxicity.

In employing oxyphenarsine in treating a human patient, the drug may be administered intravenously in an amount of about 0.5 to 1.5 milligrams per kilogram of patient body weight, and preferably about 0.8 to 1.2 milligrams per kilogram of body weight. The drug preferably is given in small doses within these ranges and is gradually increased until full dosages are attained. The drug preferably is given rapidly intravenously at least 1 to 2 times a week dependent on patient tolerance. The duration of treatment will generally be monitored by the antiviral effect and tolerance.

It will be appreciated, therefore, that the present invention has provided an effective means for treating the human immunodeficiency virus. This is accomplished employing a medication which is nontoxic and does not have any other significant undesired side effects.

Whereas particular embodiments of the invention have been described above for purposes of illustration, it will be evident to those skilled in the art that numerous variations of the details may be made without departing from the invention as defined in the appended claims.

We claim:

1. A method of treating a human patient having human immunodeficiency virus comprising
   administering to said patient intravenously a dosage of oxyphenarsine therapeutically effective to inhibit immunodeficiency virus.

2. The method of treatment of claim 1 including administering said dosage at least 1 to 2 times a week.

3. The method of claim 1 including
   administering said oxyphenarsine in the amount of up to about 1 milligram per kilogram of patient body weight.

4. The method of claim 3 including
   administering said dosage about 1 to 2 times per week.

5. The method of claim 4 including
   administering said oxyphenarsine in the amount of about 0.5 to 1 milligram per kilogram of patient body weight.

6. The method of claim 1 including
   administering said oxyphenarsine in such dosage as to achieve in the patient blood serum concentration of said oxyphenarsine of about 0.12 to 6.0 micrograms per milliliter.

7. The method of claim 6 including
   administering said oxyphenarsine in such dosage as to achieve in said patient a blood serum concentration of about 0.035 to 0.7 micrograms per milliliter.

8. The method of claim 6 including
   administering said oxyphenarsine in such dosage as to achieve in said patient a blood serum concentration of about 1.2 to 6 micrograms per milliliter.

* * * * *

UNITED STATES PATENT AND TRADEMARK OFFICE
CERTIFICATE OF CORRECTION

PATENT NO. : 4,923,895
DATED : May 8, 1990
INVENTOR(S) : MONTO HO and PHALGUNI GUPTA It is certified that error appears in the above-identified patent and that said Letters Patent is hereby corrected as shown below:

Column 1, line 4, insert the following:

--Government Support: This invention was made with government support under Grant No. 5 U01 AI 27672 and Contract No. N01-AI-72632 awarded by the National Institutes of Health, National Institute of Allergy and Infections Diseases. The government has certain rights in the invention.--

Signed and Sealed this

Sixteenth Day of March, 1993

Attest:

STEPHEN G. KUNIN

*Attesting Officer*     *Acting Commissioner of Patents and Trademarks*